US012678037B2

(12) United States Patent
    Alotaibi

(10) Patent No.:  US 12,678,037 B2
(45) Date of Patent:      Jul. 14, 2026

(54) DENTAL FIXED MIRROR WITH REFERENCE POINT

(71) Applicant: KING SAUD UNIVERSITY, Riyadh (SA)

(72) Inventor: Abdulaziz Ghassab Alotaibi, Riyadh (SA)

(73) Assignee: KING SAUD UNIVERSITY, Riyadh (SA)

( * ) Notice:  Subject to any disclaimer, the term of this patent is extended or adjusted under 35 U.S.C. 154(b) by 0 days.

(21) Appl. No.: 18/224,731

(22) Filed: Jul. 21, 2023

(65) Prior Publication Data

US 2025/0025037 A1      Jan. 23, 2025

(51) Int. Cl.
     *A61B 1/247*          (2006.01)
(52) U.S. Cl.
     CPC ................................... *A61B 1/247* (2013.01)
(58) Field of Classification Search
     CPC ....... A61B 1/247; A61B 5/4547; A61B 1/253; A61C 5/44; A61C 5/82; A61C 5/80
     See application file for complete search history.

(56) References Cited

U.S. PATENT DOCUMENTS

| | | | |
|---|---|---|---|
| 369,114 A | 8/1887 | Knapp | |
| 470,211 A | 3/1892 | Phillips | |

| | | | | |
|---|---|---|---|---|
| 1,397,090 A | * | 11/1921 | Dimas | ..................... A61B 1/247 |
| | | | | 433/30 |
| 5,230,622 A | | 7/1993 | Brossolt | |
| 5,458,486 A | * | 10/1995 | Ballard | .................. A61B 1/247 |
| | | | | 433/30 |
| 6,390,814 B1 | * | 5/2002 | Gardiner | ................ A61C 1/082 |
| | | | | 433/102 |
| 10,335,022 B1 | | 7/2019 | Bin Saleh | |
| 2023/0122799 A1 | | 4/2023 | Al Safer et al. | |

FOREIGN PATENT DOCUMENTS

| | | | | |
|---|---|---|---|---|
| WO | WO-2019171381 A1 | * | 9/2019 | |
| WO | WO-2019174839 A1 | * | 9/2019 | ............. A61C 17/08 |

* cited by examiner

*Primary Examiner* — Heidi M Eide
*Assistant Examiner* — Shannel Nicole Belk
(74) *Attorney, Agent, or Firm* — Nath, Goldberg & Meyer; Joshua B. Goldberg

(57)                    ABSTRACT

A dental mirror with a reference point that includes an adjustable fixed mirror and reference point for endodontic treatment. This tool is attached to the bow of a tooth clamp by a clip and is removable. It enables a practitioners to hold a handpiece with one hand and the suction with the other. Practitioners will have an indirect view of the upper teeth using the mirror that is attached to the bow of the clamp. They can use the reference point if there is no clear point of reference for example in a badly decayed tooth or unclear reference point like in an inclined remaining tooth structure.

11 Claims, 3 Drawing Sheets

WORKING LENGTH

TOOTH LENGTH

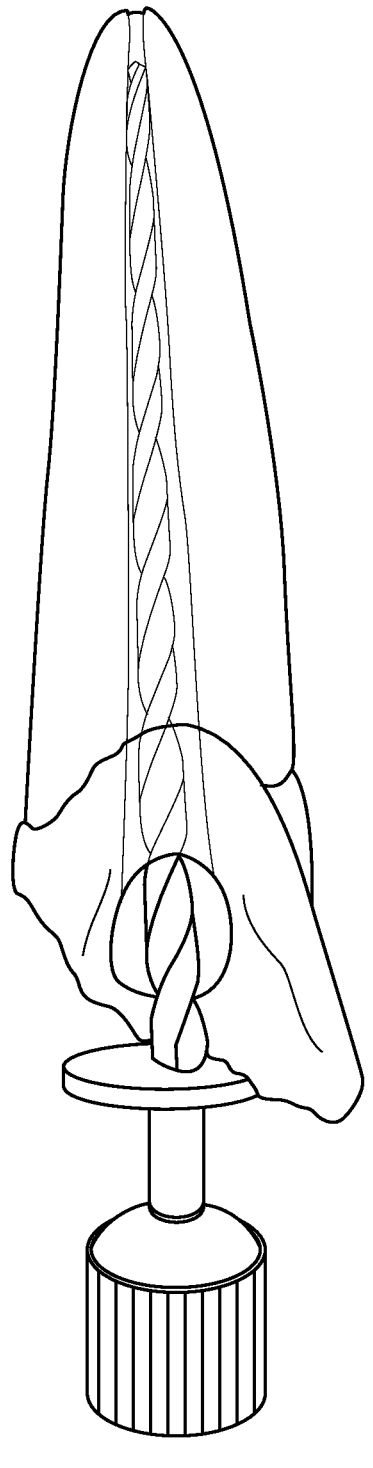
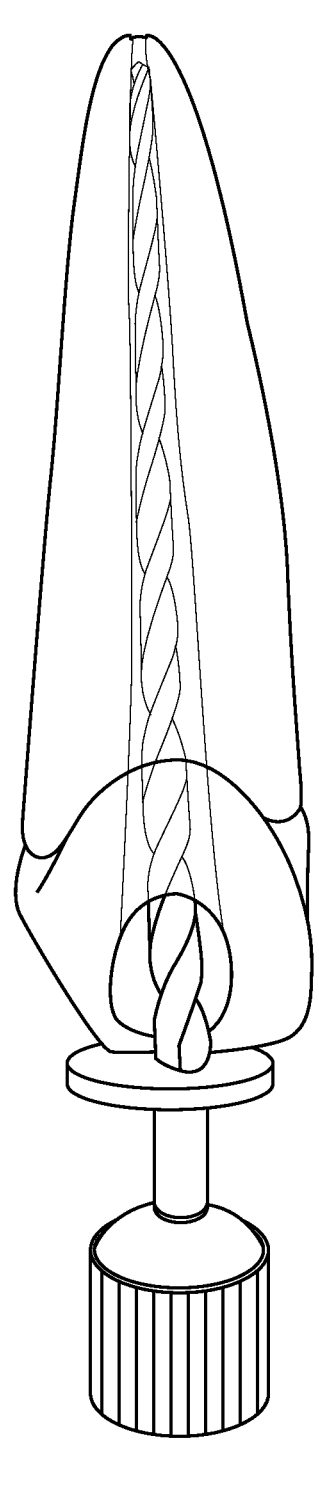
FIG. 3A
FIG. 3B

DENTAL FIXED MIRROR WITH REFERENCE POINT

BACKGROUND

1. Field

The present disclosure relates to dental procedures, and particularly to dental procedures such as root canals and fillings for teeth.

2. Description of the Related Art

When performing dental procedures such as root canals or fillings for teeth, a practitioner holds a handpiece (drill) with one hand and a hand mirror with the other hand. Since there is no one to help the practitioner in suctioning the water from the handpiece, the practitioner has to stop frequently to suction the water and clean the hand mirror.

Some practitioners do not use a mirror because of this problem, so they work by looking directly at the upper teeth without a mirror. This causes them to strain their necks and their backs in awkward positions, which is painful and unhealthy for the neck and back.

SUMMARY

There is a need for an instrument that can relieve a practitioner, dentists and endodontists, from having to hold a mirror, when performing a procedure such as a root canal or providing fillings in teeth. If a dentist or endodontist does not have to worry about holding a hand mirror, the other hand will be free to perform other tasks. For instance, a practitioner will be able to use one of their hands to hold the suction, relieving the assistant from holding the suction for them. The assistant will be able to bring and prepare the necessary tools and materials for treatment. Consequently, patient treatment time will be shortened and the practitioner will be able to treat more patients.

A dental mirror with reference point as described herein includes a mirror clip attached to a tooth clamp, and a rod having a first end and a second end. The first end of the rod is connected to the mirror clip. A mirror is connected to the second end of the rod. A reference point extends from the rod to a top portion of the tooth, and provides a point of reference for a user to visualize the top of the tooth and assist in depth perception. The reference point is especially useful when there is no clear reference point, for example in a badly decayed tooth, or unclear reference point, for example in an inclined remaining tooth structure.

The rod can include a first ball and socket joint allowing for adjustment of the mirror. The distance between the first ball and socket joint and the mirror clip can be about 3 mm in one embodiment.

The rod can further include a second ball and socket joint, spaced apart from the first ball and socket joint, allowing for adjustment of the mirror at more than one angle. The distance between the first ball and socket joint and the second ball and socket joint can be about 5 mm in one embodiment.

The reference point can include a first reference point ball and socket joint, and a second reference point ball and socket joint spaced apart from the first reference point ball and socket joint. The distance between the rod and the first reference point ball and socket joint can be about 3 mm in one embodiment.

In an embodiment, the mirror can be about 2 cm in diameter.

In an embodiment, the rod can be made of stainless steel. The reference point can terminate at an end made of sheet metal that is flat and cylindrical.

These and other features of the present subject matter will become readily apparent upon further review of the following specification.

BRIEF DESCRIPTION OF THE DRAWINGS

FIG. 3A is an illustration of an inclined tooth structure.

FIG. 3B is an illustration of an inclined tooth structure after removal of some tooth structure.

Similar reference characters denote corresponding features consistently throughout the attached drawings.

DETAILED DESCRIPTION OF THE PREFERRED EMBODIMENTS

A visual aid to a dental student, dentist, or endodontist for performing dental treatment procedures accurately and easily includes a mirror and a reference point. When performing a root canal treatment or providing fillings in teeth, a handpiece is held with one hand and a hand mirror is held with the other hand. Additionally, one has to also provide suction from another handpiece. A problem arises in that when suctioning water from the handpiece a student or practitioner has to stop frequently to suction off the water and clean the hand mirror. Accordingly, some students and/or practitioners skip usage of the mirror, thus relying upon direct visual inspection of the surgical site which often times requires positioning one's head, neck, or back in an uncomfortable position that puts strain and incurs pain while trying to maintain a particular uncomfortable position.

A dental mirror with a reference point that includes an adjustable fixed mirror and reference point for endodontic treatment is attached to the bow of a dental clamp (used to fix the rubber dental dam used in treating the root canals, and restoring teeth) by a clip and is removable. This tool enables a practitioners to hold a handpiece with one hand and the suction with the other. The practitioners will have an indirect view of the upper teeth using the mirror that is attached to the bow of the clamp. The practitioner can use the reference point if there is no clear reference point, for example in a badly decayed tooth, or unclear reference point, for example in an inclined remaining tooth structure.

Figure 1:
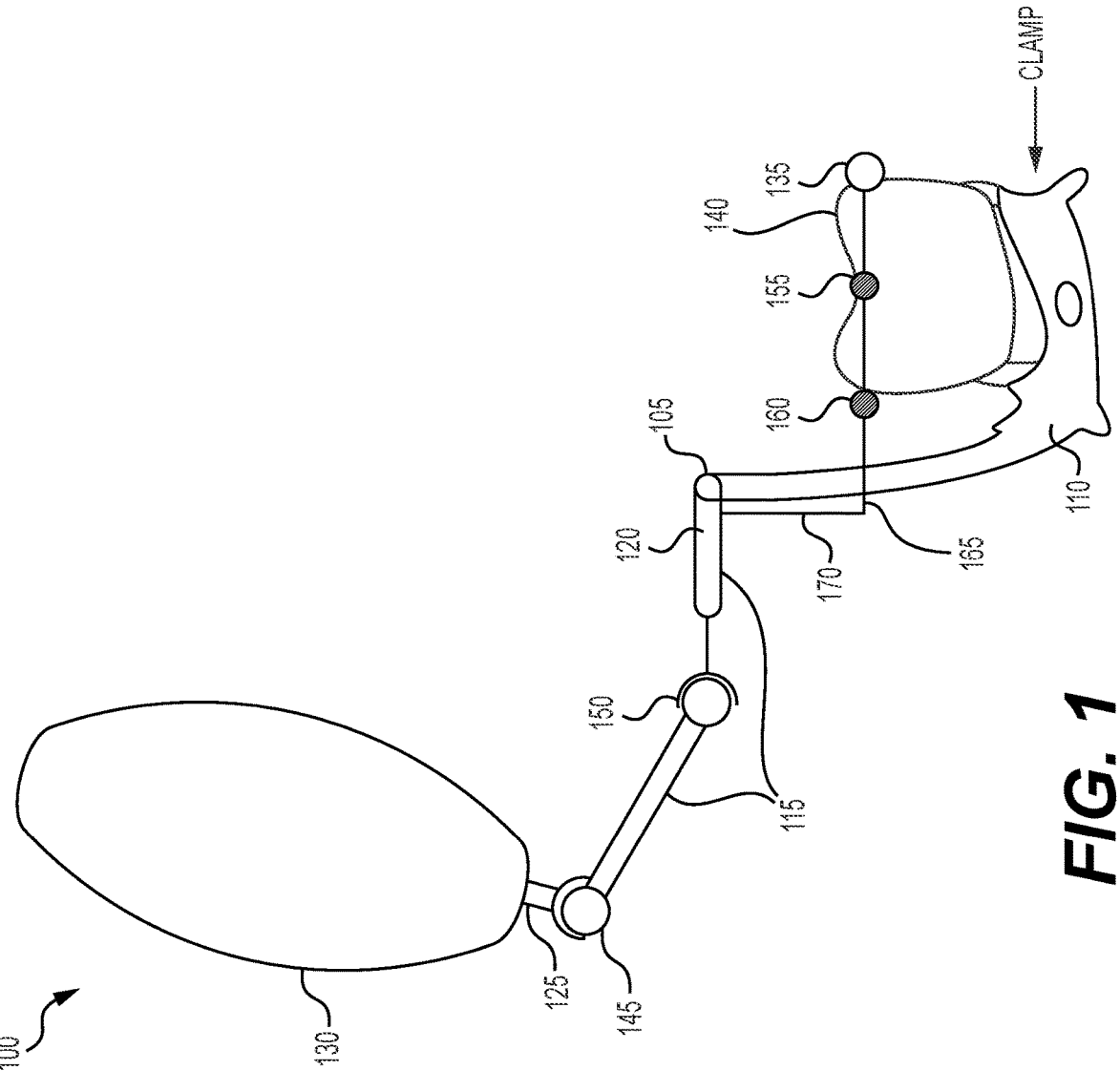
FIG. 1 is an illustration of a dental mirror with a reference point.

FIG. 1 is an illustration of a dental mirror with a reference point. A dental mirror with reference point 100 includes a mirror clip 105 attached to a tooth clamp 110, and a rod 115 having a first end 120 and a second end 125. The first end 120 of the rod 115 is connected to the mirror clip 105. A mirror 130 is connected to the second end 125 of the rod 115. A reference point 135 extends from the rod 115 to a top portion of a tooth 140, and provides a point of reference for a user to visualize the top of the tooth and assist in depth perception. The extension of the reference point is provided by a generally L-shaped extension arm made of two segments. The first segment 170 of the L-shaped extension arm extends from the first end 120 of the rod 115 and joins with a second segment 165 which extends at a right angle along the portion of the tooth 140. The reference point is especially useful when there is no clear reference point for example in a badly decayed tooth or unclear reference point like an inclined remaining tooth structure.

The rod 115 can include a first ball and socket joint 145 allowing for adjustment of the mirror. In an embodiment, the distance between the first ball and socket joint 145 and the mirror clip 105 is about 3 mm.

The rod 115, in other embodiments, further includes a second ball and socket joint 150, spaced apart from the first ball and socket joint 145, allowing for adjustment of the mirror at more than one angle. In an embodiment, the distance between the first ball and socket joint 145 and the second ball and socket joint 150 is about 5 mm.

The reference point 135 can include a first reference point ball and socket joint 155, and a second reference point ball and socket joint 160 spaced apart from the first reference point ball and socket joint 155. In an embodiment, the distance between the rod 115 and the first reference point ball and socket joint 155 is about 3 mm The mirror 130, in some embodiments, is about 2 cm in diameter.

The rod 115 can be made of stainless steel.

The reference point 135, in some embodiments, has a terminal end made of sheet metal that is flat and cylindrical.

Figure 2:
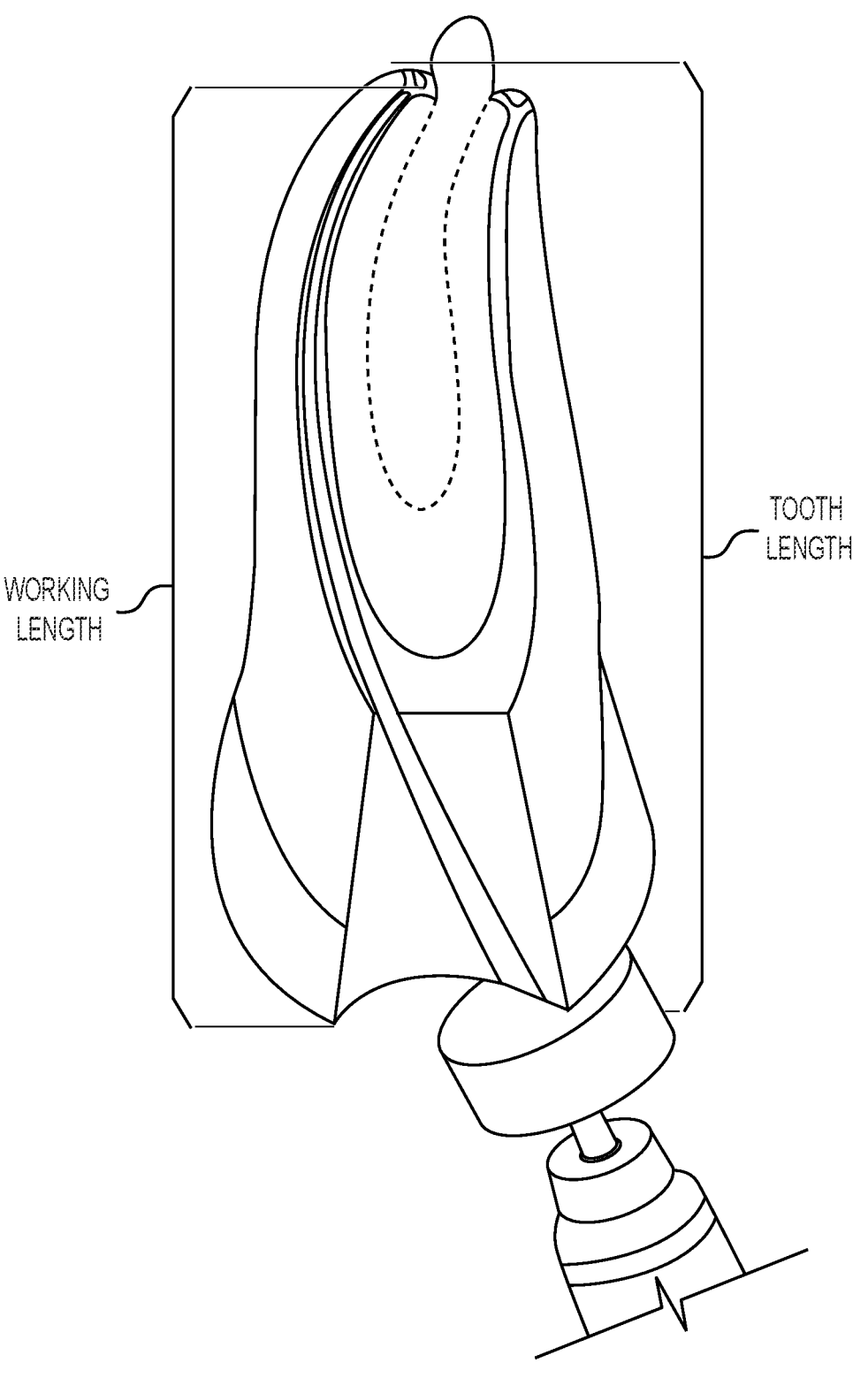
FIG. 2 is an illustration of a tooth showing working length and tooth length.

One of the important factors in the success of root canal treatment is the accurate determination of the working length (WL). The definition of working length is the distance between a coronal reference point to the point in the apex of the tooth at which canal preparation cleaning and obturation should end (see FIG. 2).

Accurate determination of working length prevents UNDER INSTRUMENTATION which could leave tissues and debris in the apical segment, or OVER INSTRUMENTATION which could cause patient discomfort, damage periapical tissue, or potentially cause an infection or cyst development from the placement of irritating materials beyond the apex.

To have an accurate WL the user should have a clear coronal reference point. Usually, the incisal edge in anterior teeth and the cusp tip in posterior teeth is used. Sometimes this is not possible in the case of a badly decayed tooth or in case you have difficulties in finding a clear coronal reference point like in an inclined remaining tooth structure (see FIG. 3A). In this case, it is necessary to remove sound tooth structure to make it flat for an easy reference point (see FIG. 3B).

Reference point 135, as illustrated in FIG. 1, will solve this problem and can be used as a point of reference without removing any sound tooth structure. Reference point 135 can also be used when there is no nearby tooth structure to give an accurate WL, and consequently provide a better treatment outcome.

It is to be understood that the dental mirror with reference point is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A dental mirror with reference point, comprising:

a mirror clip attached to a tooth clamp;

a rod having a first end and a second end, the first end connected to the mirror clip;

a mirror connected to the second end of the rod;

an L shaped extension arm is configured to extend from the rod to a top portion of the tooth;

at least one reference point connected to the L-shaped extension arm, the at least one reference point is configured to be positioned at the top portion of the tooth, and the at least one reference point providing a point of reference for a user to visualize the top of the tooth and assist in depth perception and determine a working length for the tooth, wherein providing the point of reference is accomplished without a need for a flat surface on the top portion of the tooth and without a need to remove any sound tooth structure from the tooth, wherein the at least one reference point comprises a first reference point ball and socket joint, wherein the working length is a distance between a coronal reference point of the tooth to a point in an apex of the tooth at which a canal preparation cleaning and obturation of the tooth should end.

2. The dental mirror as recited in claim 1, wherein the rod comprises a first ball and socket joint allowing for adjustment of the mirror.

3. The dental mirror as recited in claim 2, wherein a distance between the first ball and socket joint and the mirror clip is about 3 mm.

4. The dental mirror as recited in claim 3, wherein the rod further comprises a second ball and socket joint, spaced apart from the first ball and socket joint, allowing for adjustment of the mirror at more than one angle.

5. The dental mirror as recited in claim 4, wherein a distance between the first ball and socket joint and the second ball and socket joint is about 5 mm.

6. The dental mirror as recited in claim 1, wherein a distance between the rod and the first reference point ball and socket joint is about 3 mm.

7. The dental mirror as recited in claim 1, wherein the at least one reference point further comprises a second reference point ball and socket joint spaced apart from the first reference point ball and socket joint.

8. The dental mirror as recited in claim 1, wherein the mirror is about 2 cm in diameter.

9. The dental mirror as recited in claim 1, wherein the rod is made of stainless steel.

10. The dental mirror as recited in claim 1, wherein the at least one reference point further comprising an additional reference point that terminates at an end made of sheet metal.

11. The dental mirror as recited in claim 1, wherein the at least one reference point further comprising an additional reference point that terminates at an end that is flat and cylindrical.

* * * * *